(12) United States Patent
Buchwald-Werner et al.

(10) Patent No.: US 8,993,005 B2
(45) Date of Patent: Mar. 31, 2015

(54) FOOD COMPOSITIONS COMPRISING LEMON BALM EXTRACTS

(75) Inventors: Sybille Buchwald-Werner, Düsseldorf (DE); Claudia Scholz, Darmstadt (DE); Ralf Zink, Langenfeld (DE); Matthias Sass, Oftersheim (DE)

(73) Assignee: Rudolf Wild GmbH & Co. KG, Eppelheim (DE)

( * ) Notice: Subject to any disclaimer, the term of this patent is extended or adjusted under 35 U.S.C. 154(b) by 33 days.

(21) Appl. No.: 12/738,510

(22) PCT Filed: Oct. 8, 2008

(86) PCT No.: PCT/EP2008/008472
§ 371 (c)(1),
(2), (4) Date: Aug. 17, 2010

(87) PCT Pub. No.: WO2009/056208
PCT Pub. Date: May 7, 2009

(65) Prior Publication Data
US 2010/0297266 A1    Nov. 25, 2010

(30) Foreign Application Priority Data
Oct. 17, 2007   (EP) .................................. 07020260

(51) Int. Cl.
| A61K 36/00 | (2006.01) |
| A23L 1/30 | (2006.01) |
| A23C 9/13 | (2006.01) |
| A23C 9/152 | (2006.01) |
| A23L 1/222 | (2006.01) |
| A61K 36/53 | (2006.01) |

(52) U.S. Cl.
CPC ............... *A23L 1/3002* (2013.01); *A23C 9/13* (2013.01); *A23C 9/152* (2013.01); *A23L 1/2225* (2013.01); *A61K 36/53* (2013.01)
USPC ........................................................ 424/725

(58) Field of Classification Search
None
See application file for complete search history.

(56) References Cited

U.S. PATENT DOCUMENTS

| 4,354,035 | A * | 10/1982 | Christ et al. ..................... 560/75 |
| 6,340,478 | B1 * | 1/2002 | Blatt et al. ...................... 424/489 |
| 6,596,763 | B1 * | 7/2003 | Thormar et al. .............. 514/506 |
| 8,324,276 | B2 * | 12/2012 | Bryhn ........................... 514/560 |
| 2003/0012824 | A1 | 1/2003 | Ott et al. |
| 2008/0187606 | A1 | 8/2008 | Kim et al. |

FOREIGN PATENT DOCUMENTS

| HU | 208255 B | * | 9/1993 |
| JP | 11215973 | | 8/1999 |
| JP | 2000072685 A | * | 3/2000 |
| JP | 2003/245048 | | 9/2003 |
| JP | 2005/232045 | | 9/2005 |
| WO | WO-2006/042928 | | 4/2006 |
| WO | WO-2007/040377 | | 4/2007 |

OTHER PUBLICATIONS

Kennedy et al, Modulation of mood and cognitive performance following acute administration of single doses of *Melissa officinalis* (Lemon balm) with human CNS nicotinic and muscarinic receptor-binding properties, Neuropsychopharmacology (2003) vol. 28, No. 10, pp. 1871-1881.*

Kuehn et al, Occurrence of free and esterified lipoxygenase products in leaves of *Glechoma hederacea* L. and other Labiatae. European journal of biochemistry / FEBS, (Dec. 8, 1989 vol. 186, No. 1-2, pp. 155-162.*

Alkam et al, A natural scavenger of peroxynitrites, rosmarinic acid, protects against impairment of memory induced by Abeta(25-35). Behavioural brain research, (Jun. 18, 2007) vol. 180, No. 2, pp. 139-145.*

Machine translation of JP-11215973, 6 pages.

* cited by examiner

*Primary Examiner* — Qiuwen Mi
(74) *Attorney, Agent, or Firm* — Servilla Whitney LLC

(57) ABSTRACT

Disclosed are food compositions, comprising aqueous extracts of *Melissa officinalis* (Lemon balm) and/or its active principle rosmarinic acid. Methods of preparing a food composition, and of making a medicament, both methods comprising rosmarinic acid and/or aqueous extracts of *Melissa officinalis*, are also disclosed.

6 Claims, 2 Drawing Sheets

FOOD COMPOSITIONS COMPRISING LEMON BALM EXTRACTS

CROSS REFERENCE TO RELATED APPLICATIONS

This application is the National Stage entry of PCT/EP2008/008472, filed Oct. 8, 2008, which claims priority to European Patent application number EP07020260, filed Oct. 17, 2007, both of which are incorporated herein by reference in their entireties.

FIELD OF THE INVENTION

The present invention is related to the area of food compositions and refers to new products comprising botanical extracts for fighting the symptoms of stress, for enhancement of mood and improvement of cognitive functions.

BACKGROUND OF THE INVENTION

Stress is commonly counted to the social factors associated both with the development of our global society. Life style particularly in the so-called industrial countries becomes faster and faster and consequently the number of people complaining to suffer from lack of mental performance, alertness and contentment is rising.

In medical terms, stress is the disruption of homeostasis through physical or psychological stimuli. Stressful stimuli can be mental, physiological, anatomical or physical reactions. Responses to stress include adaptation, psychological coping such as stress management, anxiety, and depression. Where stress enhances function (physical or mental, such as through strength training or challenging work) it may be considered eustress. Persistent stress that is not resolved through coping or adaptation may lead to escape (anxiety) or withdrawal (depression) behavior. The fulcrum of the stress response is a disparity between experience and personal expectations and resources. A person living in a fashion consistent with personally-accepted expectations has no stress even if the conditions might be interpreted as adverse from some outside perspective—rural people may live in comparative poverty, and yet be unstressed if there is a sufficiency according to their expectations. If there is chronic disparity between experience and expectations, stress may be relieved by adjustment of expectations to meet the ongoing experiences or conditions.

The neurochemistry of the general adaptation syndrome is now believed to be well understood, although much remains to be discovered about how this system interacts with others in the brain and elsewhere in the body. The body reacts to stress first by releasing the catecholamine hormones, epinephrine (adrenaline EP) and norepinephrine (noradrenaline), and the glucocorticoid hormones, cortisol and cortisone. The hypothalamic-pituitary-adrenal axis (HPA) is a major part of the neuroendocrine system, involving the interactions of the hypothalamus, the pituitary gland, and the adrenal glands. The HPA axis is believed to play a primary role in the body's reactions to stress by balancing hormone releases from the adrenaline-producing adrenal medulla, and from the corticosteroid-producing adrenal cortex. Stress can significantly impact many of the body's immune systems, as can an individual's perceptions of, and reactions to, stress. The term psychoneuroimmunology is used to describe the interactions between the mental state, nervous and immune systems, as well as research on the interconnections of these systems.

The problem underlying the present invention has therefore been to provide new compositions, particular food products comprising botanical ingredients for the stimulation of moods, improvement of cognitive performance and in particular for fighting initial symptoms of stress.

DETAILED DESCRIPTION OF PREFERRED EMBODIMENTS

The present invention refers to food compositions, comprising aqueous extracts of *Melissa officinalis* (Lemon balm) or its active principle rosmarinic acid.

Surprisingly it has been demonstrated in single blind study that water based extracts of Lemon balm, in contrast to former published studies that concentrate on the essential oil fraction, or its active principle rosmarinic acid are suitable to stimulate moods, in particular for fighting symptoms of stress, to improve concentration and alertness, to increase contentment and to decrease anger. Former studies concentrate on the essential oil fractions. The extracts, however, can be easily incorporated into various types of food products, either as the extract itself or in encapsulated form.

Lemon Balm

*Melissa officinalis* L. (Lemon balm) is a traditional herbal medicine, well know as a mild sedative to initiate sleep. Records of its use as a sedative, anti-spasmodic and antibacterial agent date back over 2000 years. Reference is made to EP 0501591 B1 (Pure Holding Company) referring to an herbal extract composition comprising a *Melissa* species extract, an *Avena* species extract and a *Tilia* species extract, and a process for preparing it. EP 0762837 B1 (J. P. Schür) discloses a microbicide composition containing benzyl alcohol and at least one additional microbicidal GRAS (generally regarded as safe) flavouring agent, e.g. rosmarinic acid. The composition is used for treating the surfaces of microbially perishable products and/or their environment. U.S. Pat. No. 6,306,450 (Hauser) concerns a citrus-flavoured composition containing citral as flavouring compound, and a water-soluble plant extract comprising a caffeic acid derivative as stabilizer. In a preferred embodiment, the stabilizer is an extract of *Melissa officinalis*. U.S. Pat. No. 6,576,285 (Sunpure) relates to a beverage emulsion for use in the production of a cholesterol lowering beverage comprising at least 60% water, at least about 20% emulsifier, at least about 15% sterol esters. In a preferred embodiment, the composition further contains an antioxidant, for example, rosmarinic acid. Finally, U.S. Pat. No. 6,828,310 (Grain Processing Corp.) discloses a composition comprising reduced maltodextrines, which preserve a material susceptible to degradation. In a preferred embodiment, the material may be an antioxidant, e.g. rosmarinic acid, among others.

In Europe, it was first introduced to Spain by Moors in the seventh century. Lemon balm leaves are long, broadly oval, with irregularly crenate or serrate margin. They have a dark-green, slightly pubescent upper surface and thin prominent venation on the lower surface. Lemon balm is also characterised by its spicy, aromatic odour, reminiscent of lemon. The aqueous extracts comprise several active principles, mainly flavonoids and polyphenolic compounds, mostly rosmarinic acid.

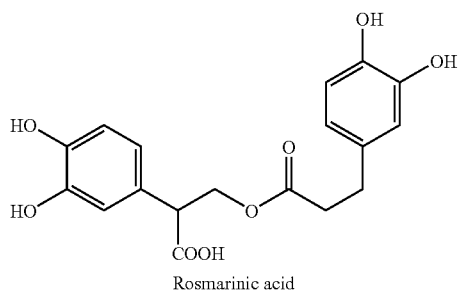 [SMILES: O=C(CCc1ccc(O)c(O)c1)OCC(C(=O)O)c1ccc(O)c(O)c1]

Rosmarinic acid

Figure 1:
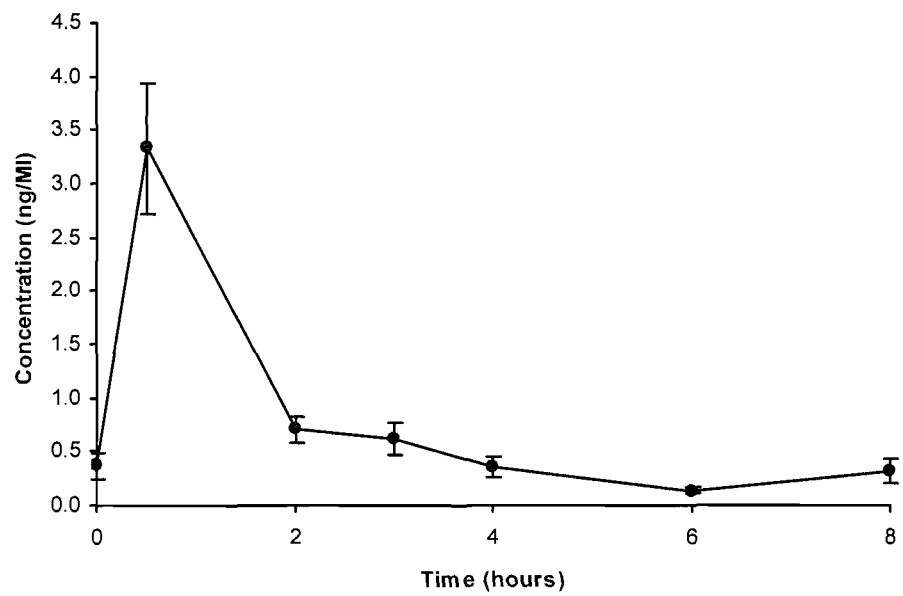
FIG. 1 shows a graph of the averaged concentration of rosmarinic acid versus time in patients following oral administration of Lemon Balm.
Figure 2:
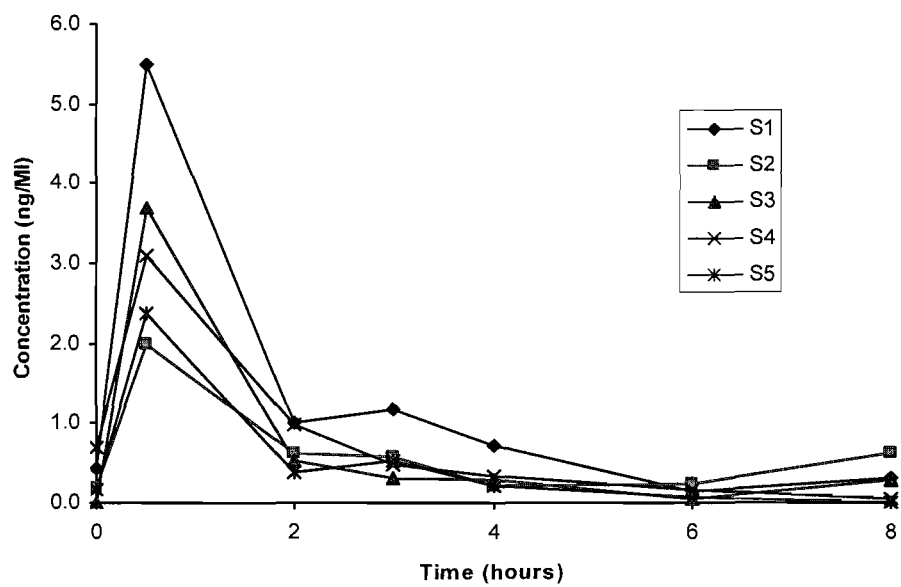
FIG. 2 shows a graph of the individual concentrations of rosmarinic acid in patients following oral administration of Lemon Balm.
Figure 3:
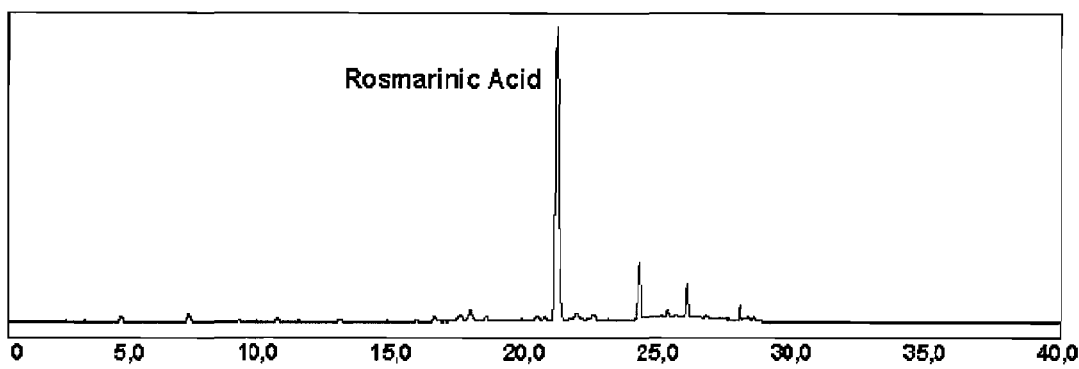
FIG. 3 shows an HPLC fingerprint of Plantalin® Lemon Balm.

A HPLC fingerprint of an extract available from Cognis GmbH in the market is shown in FIG. 3. Usually, the extracts comprise rosmarinic acid at a level of 1 to 5% b.w. It is preferred to add the lemon balm extract in an amount of about 1 to about 50, more preferably about 2 to about 25 and most preferably about 10 to about 15 g/L (which would be equivalent to about 0.01 to about 2.5 g rosmarinic acid).

Food Compositions

Said Lemon balm extracts or said rosmarinic acid can be incorporated in each type of food composition dedicated for oral consumption for example in the form of a beverage, a bar or a confectionary. In a preferred embodiment of the present invention said food composition is a fruit drink, a milk product or a yoghurt.

In another preferred embodiment of the present invention said food products is a juice derived from different fruits, containing solely original and natural soluble sugars of each used fruit, but is free of soluble sugars species coming from the breaking down of polysaccharides or more complex carbohydrates. Such compositions usually represent liquids, e.g. concentrated syrups from 65° Brix until maximum 79° Brix showing a very low glycemic index of about 34. A prominent example found in the market is Fruit Up®, supplied by Wild GmbH.

Additional Ingredients

In a further preferred embodiment of the present invention the Lemon balm extracts can be combined with further ingredients, as for example physiologically active fatty acids for active weight management and/or sterols or sterol esters for reducing cholesterol content in serum.

Physiologically Active Fatty Acids, their Salts and their Esters

A common criterion for fatty acids with physiological activity, which represent component (b), is a fat chain having a sufficient number of carbon atoms providing a lipophilic behaviour that allows the molecule to pass through the gastrointestinal tract of the body and having a sufficient number of double bonds. Therefore, said fatty acids usually comprise 18 to 26 carbon atoms and 2 to 6 double bonds.

In a first embodiment of the present invention conjugated linoleic acid (CLA) or its alkaline or alkaline earth salts and esters, preferably, their calcium salts and their esters with lower aliphatic alcohols having 1 to 4 carbon atoms—or their glycerides, specially their triglycerides come into account.

Conjugated linoleic acid (CLA) represents a commercially available product which usually is obtained by base-catalysed isomerisation of sunflower oil or their respective alkyl esters and subsequent isomerisation in the presence of enzymes. CLA is an acronym used for positional and geometric isomers deriving from the essential fatty acid linoleic acid (LA, cis-9,cis-12-octadecadienoic acid, 18:2n-6). From a physiological point of view the use of the cis-9,trans-11 isomer according to the present invention is of special importance having at least 30, preferably at least 50, and most preferably at least 80% b.w. of said cis-9,trans-11 isomer—based on the total CLA content of the crude mixture. In addition, it has been found advantageous if the content of the trans-10,cis-12 isomer is at most 45, preferably at most 10% b.w. and most preferably less than 1% b.w., and the sum of 8,10-, 11,13- and trans,trans-isomers in total is less than 1% b.w.—again based on the total CLA content. Such products can be found in the market, for example, under the trademark Tonalin® CLA-80 (Cognis).

In a second embodiment also so-called omega-3 fatty acids can come into account, which typically comprise 18 to 26, preferably 20 to 22 carbon atoms and at least 4 and up to 6 double bonds. Also these molecules are very well known from the art and can be obtained by standard methods of organic chemistry, for example, via transesterification of fish oils, followed by urea precipitation of the alkyl esters thus obtained and a final extraction using non-polar solvents as described in the German patent DE 3926658 C2 (Norsk Hydro). Fatty acids thus obtained are rich in omega-3 (all-Z)-5,8,11,14,17-eicosapentanoic acid (EPA) C 20:5 and (all-Z)-4,7,10,13,16,19-docosahexanoic acid (DHA) C 22:6. Such products can be found in the market under the trademark Omacor® (Pronova).

In a third embodiment also linoleic acid, vaccinic acid (trans 11-octadecenoic acid), cis-hexadecenoic acid (obtained, for example, from the plant *Thunbergia alata*), eicosapentaenoic acid, docosahexaenoic acid and mixtures thereof can be used.

In addition, said physiologically active fatty acid esters can not only be used in form of their lower alkyl esters or glycerides. An additional well preferred embodiment of the present invention relates to compositions comprising esters of said fatty acids with sterols. Like glycerides, sterol esters are easily resorbed and split by the human body. However, a significant advantage comes from the fact that the cleavage of the ester bond releases a second molecule with health promoting properties. To avoid unclarities, the phrases "sterol", "stanol", and "sterin" shall be used as synonyms defining steroids showing a single hydroxyl group linked to the C-3. In addition, sterols which consist of 27 to 30 carbon atoms, may show a double bond, preferably in 5/6 position. According to the present invention, esters of CLA or omega-3 fatty acids with β-sitosterol or its hydrogenation product β-sitostanol are preferred.

Sterols and Sterol Esters

Sterols—also called sterins—represent steroids showing a single hydroxyl group linked to the C-3. In addition sterols, which consist of 27 to 30 carbon atoms, may show a double bond, preferably in 5/6 position. The hydrogenation of the double bond ("hardening") leads to sterols which are usually called stanols. The figure below shows the structure of the best known member of the sterol family, cholesterol, which belongs to the group of zoosterols.

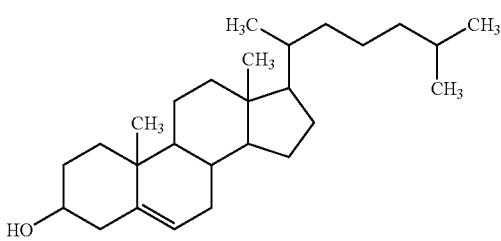 [SMILES: CC(C)CCCC(C)C1CCC2C3CC=C4CC(O)CCC4(C)C3CCC12C]

Due to their superior physiological activity, the plant sterols, so-called phytosterols, like ergosterol, stigmasterol, and especially sitosterol and its hydrogenation product sitastanol, are the preferred species. In addition instead of the sterols or stanols their esters with saturated or unsaturated fatty acids having 6 to 26 carbon atoms and up to 6 double bonds can be used. Typical examples are the esters of β-sitosterol or β-sitostanol with capric acid, caprylic acid, 2-ethylhexanoic acid, caprinic acid, lauric acid, isotridecylic acid, myristic acid, palmitic acid, palmoleic acid, stearic acid, isostearic acid, oleic acid, elaidinic acid, petroselinic acid, linolic acid, linoleic acid, elaeostearic acid, arachidonic acid, gadoleinic acid, behenic acid and erucic acid.

Said aqueous lemon balm extracts/rosmarinic acid and said additional ingredient can be used for making the food products in weight proportions of 1:9 to 9:1 and preferably 4:6 to 6:4.

Microcapsules

Usually the lemon balm extracts or the rosmarinic acid are added to the food products either as an aqueous solution or a spray dried powder. In order to improve stability of the compositions or for simply for esthetical reasons it might be desirous to add the extracts to the food compositions in a micro-encapsulated form.

"Microcapsules" are understood to be spherical aggregates with a diameter of about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone.

Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

The active principles are released from the microcapsules by mechanical, thermal, chemical or enzymatic destruction of the membrane, normally during the use of the preparations containing the microcapsules. From the state of the art also a huge number of different processes for the encapsulation of active principles are known: WO 99/043426; WO 01/001928; WO 01/001929; WO 01/066240; WO 01/066241; WO 01/098578; WO 02/0178859; WO 02/0178868; WO 02/076607; WO 02/076606; WO 02/077359; WO 02/077360; WO 03/022419; WO 03/093571; WO 03/092664; WO 03/092880; WO 04/091555; WO 04/106621; EP 1064911 B1; EP 1064912 B1; EP 1077060 B1; EP 1101527 B1; EP 1223243 B1; EP 1243318 B1; EP 1243320 B1; EP 1243323 B1; EP 1243324 B1; EP 1254983 B1; EP 1121542 B1 all filed on behalf of Henkel KGaA, Primacare S.A. or Cognis Iberia, S.L. and herewith incorporated by reference.

Despite the fact that the state of the art a huge range of possibilities for the encapsulation of actives, methods according to which a shell is obtained by coazervation, precipitation or polycondensation of anionic and cationic polymers has been quite suitable for the formation of stable capsules. Particularly, a preferred process for the encapsulation of active principles according to the present invention is characterised in that it comprises the steps of (a) preparing a matrix from gel formers, cationic polymers and active principles;
(b) optionally dispersing said matrix in an oil phase; and
(c) treating said dispersed matrix with aqueous solutions of anionic polymers and optionally removing the in phase in the process.

Of course, anionic and cationic polymers in steps (a) and (c) can be exchanged.

Gel Formers

In the context of the invention, preferred gel formers are substances which are capable of forming gels in aqueous solution at temperatures above 40° C. Typical examples of such gel formers are heteropolysaccharides and proteins. Preferred thermogelling heteropolysaccharides are agaroses which may be present in the form of the agar agar obtainable from red algae, even together with up to 30% by weight of non-gel-forming agaropectins. The principal constituent of agaroses are linear polysaccharides of Galactose and 3,6-anhydro-L-galactose with alternate 1,3- and 1,4-glycosidic bonds. The heteropolysaccharides preferably have a molecular weight of 110,000 to 160,000 and are both odourless and tasteless. Suitable alternatives are pectins, xanthans (including xanthan gum) and mixtures thereof. Other preferred types are those which in 1% by weight aqueous solution still form gels that do not melt below 80° C. and solidify again above 40° C. Examples from the group of thermogelling proteins are the various gelatines.

Anionic Polymers

Salts of alginic acid are preferred for this purpose. The alginic acid is a mixture of carboxyl-containing polysaccharides with the following idealized monomer unit:

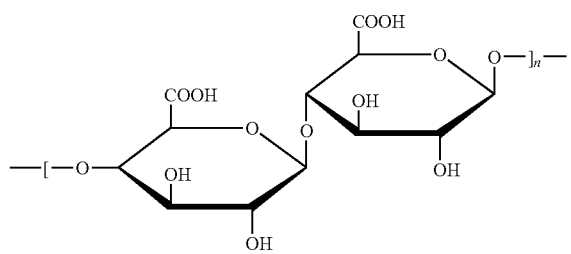

The average molecular weight of the alginic acid or the alginates is in the range from 150,000 to 250,000. Salts of alginic acid and complete and partial neutralization products thereof are understood. In particular to be the alkali metal salts, preferably sodium alginate ("algin") and the ammonium and alkaline earth metal salts. Mixed alginates, for example sodium/magnesium or sodium/calcium alginates, are particularly preferred. In an alternative embodiment of the invention, however, carboxymethyl celluloses and anionic chitosan derivatives, for example the carboxylation and above all succinylation products are also suitable for this purpose.

Cationic Polymers

Chitosans are biopolymers which belong to the group of hydrocolloids. Chemically, they are partly de-acetylated chitins differing in their molecular weights which contain the following—idealized—monomer unit:

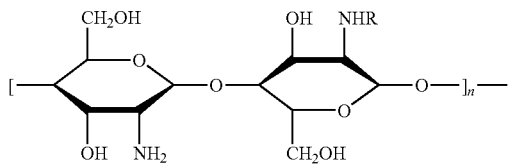

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations. Chitosans are produced from chitin, preferably from the shell residues of crustaceans which are available in large quantities as inexpensive raw materials. In a process described for the first time by Hackmann et al., the chitin is normally first de-proteinized by addition of bases, de-mineralized by addition of mineral acids and, finally, de-acetylated by addition of strong bases, the molecular weights being distributed over a broad spectrum. Preferred types are those which are disclosed in German patent applications DE 4442987 A1 and DE 19537001 A1 (Henkel) and which have an average molecular weight of 10,000 to 500,000 Dalton or 800,000 to 1,200,000 Dalton and/or a Brookfield viscosity (1% by weight in glycolic acid) below 5,000 mPas, a degree of de-acetylation of 80 to 88% and an ash content of less than 0.3% by weight. In the interests of better solubility in water, the chitosans are generally used in the form of their salts, preferably as glycolates.

In a preferred embodiment of the invention a 1 to 10 and preferably 2 to 5% by weight aqueous solution of the gel former, preferably agar agar, is normally prepared and heated under reflux. A second aqueous solution containing the cationic polymer, preferably chitosan, in quantities of 0.1 to 2 and preferably 0.25 to 0.5% by weight and the active principle in quantities of 0.1 to 25 and preferably 0.25 to 10% by weight is added in the boiling heat, preferably at 80 to 100° C.; this mixture is called the matrix. Accordingly, the charging of the microcapsules with active principles may also comprise 0.1 to 25% by weight, based on the weight of the capsules. If desired, water-insoluble constituents, for example inorganic pigments, may also be added at this stage to adjust viscosity, generally in the form of aqueous or aqueous/alcoholic dispersions. In addition, to emulsify or disperse the active principles, it can be useful to add emulsifiers and/or solubilisers to the matrix. After its preparation from gel former, cationic polymer and active principle, the matrix optionally is very finely dispersed in an oil phase with intensive shearing in order to produce small particles in the subsequent encapsulation process. It has proved to be particularly advantageous in this regard to heat the matrix to temperatures in the range from 40 to 60° C. while the oil phase is cooled to 10 to 20° C. The actual encapsulation, i.e. formation of the membrane by contacting the cationic polymer in the matrix with the anionic polymers, takes place in the third step. To this end, it is advisable to wash the matrix—dispersed in the oil phase— with an aqueous ca. 0.1 to 3 and preferably 0.25 to 0.5% by weight aqueous solution of the anionic polymer, preferably the alginate, at a temperature in the range from 40 to 100 and preferably 50 to 60° C. and, at the same time, to remove the oil phase if present. The resulting aqueous preparations generally have a microcapsule content of 1 to 10% by weight. In some cases, it can be of advantage for the solution of the polymers to contain other ingredients, for example emulsifiers or preservatives. After filtration, microcapsules with a mean diameter of preferably 1 to 3 mm are obtained. It is advisable to sieve the capsules to ensure a uniform size distribution. The microcapsules thus obtained may have any shape within production-related limits, but are preferably substantially spherical.

INDUSTRIAL APPLICATION

Another object of the present invention is directed to the use of aqueous extracts of *Melissa officinalis* or rosmarinic acid as ingredients for food compositions for fighting symptoms of stress, particularly for improving the word recognition sensitivity and alertness, for improving contentment and decreasing anger.

EXAMPLES

Pilot Study Results

The pilot study was conducted as a single centre, single blind assessment of cognitive improvement of a test food product containing the maximum level of Lemon balm extract. More particular the pilot study was performed with a panel of 5 male or female subjects aged 23-28 who considered themselves to lead a stressed lifestyle. Following screening and cognition test training, each subject consumed the test drink containing 1.8 g/200 ml of lemon balm extract (Plantalin® Lemon balm, Cognis GmbH, Germany) and cognition measurements were performed at baseline, 30 minutes, 2, 3, 4, 6, 8 and 12 hours post consumption of the test food. Blood samples for pharmacokinetics (PK) were also performed to assess the levels of rosmarinic acid and blood glucose. All cognition testing was performed post PK blood sampling.

A selection of tasks, from the CDR computerised cognitive assessment system, were selected to provide the optimal test battery to evaluate the cognitive effects of the product. Parallel forms (pen and paper exercises) of the tasks were also presented on each testing session to allow for repeated assessment by presenting different, but equivalent stimuli. All tasks were computer-controlled with information and stimuli being presented on the screen of a laptop computer. The responses were recorded via a response module containing two buttons, one marked 'NO' and the other 'YES'.

Blood samples were taken for pharmacokinetics, by a trained venepuncturist, at baseline, 30 minutes, 2, 3, 4, 6 and 8 hours post food consumption, the 12 hour samples were not taken due to equipment failure. Samples were analysed for levels of rosmarinic acid and glucose.

Methodology

1. The CDR Computerised Cognitive Assessment System

A selection of tasks from the CDR computerised cognitive assessment system has been selected providing the optimal test battery to evaluate the cognitive effects of the text product. Parallel forms of the tasks are presented on each testing session to allow for repeated assessment by presenting different, but equivalent stimuli. All tasks are computer-controlled with information and stimuli being presented on the screen of a laptop computer. The responses are recorded via a response module containing two buttons, one marked 'NO' and the other 'YES'.

2. CDR Core Battery

The battery covers the cognitive domains of attention/concentration, short term working memory, long term secondary memory, and also assesses mood. The battery takes 20-25 minutes to complete and consists of the following tasks.

(i) Attention/Concentration

Simple Reaction Time: This task measures pure response time to a simple stimulus. The volunteer is instructed to press the 'YES' response button as quickly as possible every time the word 'YES' is presented on the screen. Fifty stimuli are presented with a varying inter-stimulus interval. The task lasts about 2 minutes and the outcome measure is mean reaction time.

Choice Reaction Time: This task is similar to the Simple Reaction Time task but introduces a decision making element thus making the response times slower. Either the word 'NO' or the word 'YES' is presented on the screen and the volunteer is instructed to press the corresponding button as quickly as possible. There are 50 trials for which each stimulus word is chosen randomly with equal probability and there is a varying inter-stimulus interval. The task lasts about 2 minutes and the outcome measures are accuracy of responses and mean reaction time of accurate responses.

Digit Vigilance: This task measures the ability to sustain attention over a longer period of time. A target digit is randomly selected and constantly displayed to the right of the screen. A series of digits is then presented in the centre of the screen at the rate of 150 per minute and the volunteer is required to press the 'YES' button as quickly as possible every time the digit in the series matches the target digit. There are 45 targets in the series. The task lasts 3 minutes and the outcome measures are accuracy of responses, number of incorrect responses and mean reaction time of accurate responses.

(ii) Working Memory

Numeric Working Memory: This task measures the ability to hold and recall numeric information in short term working memory, and relies on the sub-articulatory rehearsal loop. A series of 5 digits is presented for the volunteer to hold in memory. This is followed by a series of 30 probe digits for each of which the volunteer has to decide whether or not it was in the original series and press the 'YES' or 'NO' response button as appropriate, as quickly as possible. This procedure is repeated twice more, using 2 different series and probes. The task lasts 2-3 minutes and the outcome measures are the accuracy of responses and mean reaction time of accurate responses.

Spatial Working Memory: This task measures the ability to store and retrieve spatial information from short term working memory, and relies upon the visuo-spatial scratchpad. A picture of a house is presented on the screen with 4 of its 9 windows lit. The volunteer has to memorise the position of the lit windows. For each of the 36 subsequent presentations of the house, the volunteer is required to decide whether or not the 1 window that was lit was also lit in the original presentation. The volunteer responds by pressing the 'YES' or 'NO' buttons as appropriate, as quickly as possible. The task lasts for about 3 minutes and the outcome measures are the accuracy of responses and the mean reaction time of accurate responses.

(iii) Long Term Secondary Memory

Immediate Word Recall and Delayed Word Recall: These tasks measure the ability to store and retrieve verbal information in an un-cued manner from long term memory. A list of 15 words is presented on the screen at the rate of 1 every 2 seconds for the volunteer to remember. The volunteer is then given 1 minute to recall as many of the words as possible (Immediate Word Recall). After a period of time (15-20 minutes), the volunteer is again given 1 minute to recall as many of the words as possible but without seeing them again (Delayed Word Recall). The outcome measure is the number of words accurately recalled at each part of the task.

Word Recognition: This task measures the ability to retrieve the same verbal information presented for the Word Recall tasks but this time in response to a series of cues. 15-20 minutes after the presentation of the original list of words, the original words plus 15 distracter words are presented one at a time in a randomised order. For each word the volunteer is required to indicate whether or not they recognise it as being from the original list of words by pressing the 'YES' or 'NO' button as appropriate, as quickly as possible. The task lasts about 3 minutes and the outcome measures are accuracy of responses and mean reaction time of accurate responses.

Picture Presentation and Picture Recognition: This task measures the ability to store and retrieve non-verbal information in a cued manner from long term memory. A series of 20 pictures are presented on the screen at the rate of 1 every 3 seconds for the volunteer to remember. After a period of time (15-20 minutes), the original pictures plus 20 distracter pictures are presented one at a time in a randomised order. For each picture the volunteer has to indicate whether or not they recognise it as being from the original series by pressing the 'YES' or 'NO' button as appropriate, as quickly as possible. The task lasts about 3 minutes and the outcome measures are accuracy of responses and mean reaction time of accurate responses.

(iv) Mood

Bond-Lader Visual Analogue Scales (VAS): This computerised questionnaire records aspects of mood. Sixteen 10 cm analogue scales are presented to the volunteer one at a time. For each scale, the volunteer uses the mouse to indicate on the line where they feel their mood lies at that point in time. The questionnaire takes about 2 minutes to complete and the outcome measures are self-rated alertness, calmness and contentment.

(v) Additional Pencil and Paper Questionnaires

The Profile of Mood States (POMS): This widely used 65 item adjective check asks the volunteers to rate how they have been feeling 'during the past week including today'. It produces six Factors: Tension-Anxiety, Depression-Dejection, Anger-Hostility, Vigour-Activity, Fatigue-Inertia and Confusion-Bewilderment. A score is obtained from each, and a single score of "mood disturbance" is also computed.

Spielberger State Anxiety Questionnaire: This test comprises of 2 self-reporting scales for measuring state or trait anxiety. The S-Anxiety scale (STAI Form Y-1) consists of twenty statements (numbers 1-20) that evaluate how respondents feel 'right now', at this moment. The part of the questionnaire is administered throughout the study. The T-Anxiety scale (STAI Form Y-2) consists of twenty statements (number 21-40) that assess how people generally feel. This part of the questionnaire is only administered once during the study.

Results

In the course of the study the following improvements to cognitive function and self-rated mood and alertness were observed:

Word Recognition Sensitivity Index (the ability to correctly recognise words) was improved at 2 and 6 hours.

Self-rated Alertness was improved at 3 and 4 hours.

Self-rated Contentment was improved at 8 and 12 hours.

Self-rated Anger decreased at all time points.

These findings indicate possible positive effects of the substance upon mood, and also the ability to recognise previously presented words. The results are compiled in the following tables.

TABLE 1

Word Recognition Sensitivity Index (accuracy)

| Time (hours) | S1 | S2 | S3 | S4 | S5 | Mean | SD |
|---|---|---|---|---|---|---|---|
| 0 | 0.611 | 0.204 | 0.450 | 0.341 | 0.536 | 0.428 | 0.161 |
| 0.5 | 0.536 | 0.536 | 0.536 | 0.450 | 0.600 | 0.532 | 0.053 |
| 2 | 0.502 | 0.747 | 0.475 | 0.511 | 0.804 | 0.608 | 0.155 |
| 3 | 0.536 | 0.556 | 0.536 | 0.402 | 0.402 | 0.486 | 0.077 |
| 4 | 0.475 | 0.536 | 0.215 | 0.333 | 0.475 | 0.407 | 0.131 |
| 6 | 0.402 | 0.747 | 0.502 | 0.556 | 0.804 | 0.602 | 0.169 |
| 8 | 0.536 | 0.467 | 0.402 | 0.536 | 0.694 | 0.527 | 0.109 |
| 12 | 0.339 | 0.402 | 0.467 | 0.556 | 0.402 | 0.433 | 0.082 |

TABLE 2

Bond-Lader VAS Alertness

| Time (hours) | S1 | S2 | S3 | S4 | S5 | Mean | SD |
|---|---|---|---|---|---|---|---|
| 0 | 46.6 | 47.2 | 46.3 | 55.2 | 55.6 | 50.18 | 4.778 |
| 0.5 | 75.7 | 48.6 | 39.9 | 51.4 | 53.2 | 53.76 | 13.29 |
| 2 | 65.6 | 49.2 | 51.7 | 50.0 | 48.9 | 53.08 | 7.083 |
| 3 | 79.7 | 49.7 | 55.3 | 49.6 | 57.4 | 58.34 | 12.42 |
| 4 | 86.2 | 53.8 | 44.8 | 50.9 | 55.6 | 58.26 | 16.15 |
| 6 | 72.9 | 46.6 | 41.2 | 51.8 | 47.7 | 52.04 | 12.26 |
| 8 | 55.9 | 43.1 | 35.7 | 56.9 | 52.3 | 48.78 | 9.115 |
| 12 | 42.2 | 47.8 | 55.3 | 52.2 | 52.0 | 49.90 | 5.064 |

TABLE 3

Bond-Lader VAS Contentment

| Time (hours) | S1 | S2 | S3 | S4 | S5 | Mean | SD |
|---|---|---|---|---|---|---|---|
| 0 | 78.8 | 48.0 | 57.4 | 58.6 | 49.2 | 58.40 | 12.35 |
| 0.5 | 84.2 | 48.0 | 50.6 | 54.0 | 48.6 | 57.08 | 15.34 |
| 2 | 82.8 | 46.2 | 57.0 | 54.0 | 51.4 | 58.28 | 14.27 |
| 3 | 85.2 | 47.8 | 58.6 | 55.0 | 55.2 | 60.36 | 14.43 |
| 4 | 89.8 | 48.2 | 56.6 | 57.0 | 52.8 | 60.88 | 16.55 |
| 6 | 85.4 | 50.2 | 59.2 | 55.4 | 52.0 | 60.44 | 14.37 |
| 8 | 87.2 | 52.8 | 60.6 | 57.2 | 54.0 | 62.36 | 14.21 |
| 12 | 83.6 | 54.6 | 64.6 | 62.0 | 50.6 | 63.08 | 12.77 |

TABLE 4

POMs Depression

| Time (hours) | S1 | S2 | S3 | S4 | S5 | Mean | SD |
|---|---|---|---|---|---|---|---|
| 0 | 11 | 10 | 0 | 0 | 4 | 5.0 | 5.292 |
| 0.5 | 10 | 11 | 1 | 0 | 3 | 5.0 | 5.148 |
| 2 | 10 | 11 | 0 | 0 | 4 | 5.0 | 5.292 |
| 3 | 12 | 11 | 0 | 4 | 5 | 6.4 | 5.030 |
| 4 | 9 | 8 | 0 | 0 | 4 | 4.2 | 4.266 |
| 6 | 11 | 7 | 0 | 0 | 6 | 4.8 | 4.764 |
| 8 | 8 | 7 | 0 | 0 | 4 | 3.8 | 3.768 |
| 12 | 9 | 9 | 0 | 0 | 4 | 4.4 | 4.506 |

TABLE 5

POMs Anger

| Time (hours) | S1 | S2 | S3 | S4 | S5 | Mean | SD |
|---|---|---|---|---|---|---|---|
| 0 | 13 | 2 | 3 | 0 | 5 | 4.6 | 5.030 |
| 0.5 | 6 | 1 | 1 | 0 | 3 | 2.2 | 2.387 |
| 2 | 10 | 2 | 0 | 0 | 0 | 2.4 | 4.336 |
| 3 | 9 | 2 | 0 | 2 | 3 | 3.2 | 3.421 |
| 4 | 12 | 2 | 0 | 0 | 0 | 2.8 | 5.215 |
| 6 | 8 | 2 | 0 | 0 | 0 | 2.0 | 3.464 |
| 8 | 10 | 2 | 0 | 0 | 0 | 2.4 | 4.336 |
| 12 | 8 | 0 | 0 | 0 | 1 | 1.8 | 3.493 |

Pharmacokinetic Data

TABLE 6

Blood analysis for Rosmarinic Acid

| Time (hours) | S1 | S2 | S3 | S4 | S5 | Mean | SEM |
|---|---|---|---|---|---|---|---|
| 0 | 0.4 | 0.2 | <intercept | 0.7 | 0.2 | 0.4 | 0.12 |
| 0.5 | 5.5 | 2.0 | 3.7 | 3.1 | 2.4 | 3.3 | 0.61 |
| 2 | 1.0 | 0.6 | 0.5 | 1.0 | 0.4 | 0.7 | 0.13 |
| 3 | 1.2 | 0.6 | 0.3 | 0.5 | 0.5 | 0.6 | 0.15 |
| 4 | 0.7 | 0.2 | 0.3 | 0.3 | 0.2 | 0.4 | 0.09 |
| 6 | 0.1 | 0.2 | <intercept | 0.2 | 0.1 | 0.1 | 0.03 |
| 8 | 0.3 | 0.6 | 0.3 | <intercept | <intercept | 0.3 | 0.12 |

| | Replicates | | | | | Mean | SEM |
|---|---|---|---|---|---|---|---|
| Control matrix | 1.0 | 0.6 | 0.6 | 1.1 | 0.6 | 0.8 | 0.11 |

TABLE 7

Blood Glucose results [1] [2] [3]

| Time | Subject 1 | Subject 2 | Subject 3 | Subject 4 | Subject 5 |
|---|---|---|---|---|---|
| 0 h | 2.5 | 4.24 | 3.29 | 2.92 | 3.04 |
| 0.5 h | 2.37 | 5.76 | 2.33 | 3.31 | 1.98 |
| 2 h | 1.96 | 2.76 | 2.76 | 3.86 | 1.19 |
| 3 h | 2.78 | 3.43 | 1.83 | 3.54 | 1.93 |
| 4 h | 2.94 | 3.66 | 1.84 | 2.65 | 2.94 |
| 6 h | 2.93 | 3.31 | 2.48 | 2.76 | 2.18 |
| 8 h | 3.07 | 3.01 | 2.27 | 2.9 | 3.19 |

[1] Daily QC and Reference Range for VITROS 250 Chemistry analyser
[2] Low QC = 4.17-5.00 mmol/L; 4.48 Range (4.17-5.00);
[3] High QC = 15.31-17.25 mmol/L; 16.70 Range (15.31-17.25)

What is claimed is:

1. A method for increasing alertness and/or improving word recognition sensitivity in a subject in need thereof, the method comprising administering to the subject a medicament comprising a water-based extract of *Melissa officinalis* and a pharmaceutical base, wherein the water-based extract of *Melissa officinalis* is present in an amount in the range of about 0.1 to about 50 g/L.

2. The method of claim 1, wherein the water-based extract of lemon balm is present in an amount in the range of about 2 to about 25 g/L.

3. The method of claim 1, further comprising adding physiologically active fatty acids and/or sterols or sterol esters to the pharmaceutical base.

4. The method of claim 1, wherein the water-based extract of *Melissa officinalis* is micro-encapsulated.

5. The method of claim 1, wherein the pharmaceutical base is a liquid comprising about 1.8 grams/200 mL of the aqueous extract of *Melissa officinalis*.

6. The method of claim 1, wherein the patient exhibits increased alertness and/or improved word recognition sensitivity up to about 6 hours after treatment.

* * * * *